(12) United States Patent
Below

(10) Patent No.: US 8,047,054 B2
(45) Date of Patent: Nov. 1, 2011

(54) PARTICULATE MATTER SENSOR

(75) Inventor: Matthew B. Below, Findlay, OH (US)

(73) Assignee: Fram Group IP LLC, Danbury, CT (US)

( * ) Notice: Subject to any disclaimer, the term of this patent is extended or adjusted under 35 U.S.C. 154(b) by 0 days.

(21) Appl. No.: 12/508,096

(22) Filed: Jul. 23, 2009

(65) Prior Publication Data

US 2010/0018290 A1 Jan. 28, 2010

Related U.S. Application Data

(63) Continuation-in-part of application No. 12/467,673, filed on May 18, 2009.

(60) Provisional application No. 61/083,333, filed on Jul. 24, 2008.

(51) Int. Cl.
*F01N 11/00* (2006.01)
*G01N 37/00* (2006.01)

(52) U.S. Cl. ...................................... 73/28.01; 73/866.5

(58) Field of Classification Search .................... 73/23.3, 73/28.01, 114.71, 866.5, 1, 23.32, 23.33
See application file for complete search history.

(56) References Cited

U.S. PATENT DOCUMENTS

| | | | |
|---|---|---|---|
| 4,111,778 A | | 9/1978 | Davis et al. |
| 4,199,424 A | * | 4/1980 | Teitelbaum ................... 204/428 |
| 4,314,478 A | * | 2/1982 | Beaman ...................... 73/304 C |
| 4,656,832 A | * | 4/1987 | Yukihisa et al. ................ 60/303 |
| 4,716,874 A | * | 1/1988 | Hilliard et al. ............ 123/406.14 |
| 6,192,740 B1 | * | 2/2001 | Thomas et al. ............... 73/28.01 |
| 6,634,210 B1 | * | 10/2003 | Bosch et al. ................. 73/23.33 |
| 6,758,082 B2 | | 7/2004 | Geier et al. |
| 6,971,258 B2 | | 12/2005 | Rhodes et al. |
| 7,275,415 B2 | | 10/2007 | Rhodes et al. |
| 7,644,609 B2 | * | 1/2010 | Reutiman et al. .......... 73/114.69 |
| 2007/0137177 A1 | | 6/2007 | Kittelson et al. |
| 2009/0113983 A1 | * | 5/2009 | Krafthefer ..................... 73/1.06 |

FOREIGN PATENT DOCUMENTS

| | | |
|---|---|---|
| KR | 20030094820 A | 12/2003 |
| WO | WO 9105994 A1 * | 5/1991 |
| WO | W02007050384 A2 | 5/2007 |

OTHER PUBLICATIONS

International Searching Report dated Dec. 28, 2009 for PCT/US2009/044351.
Written Opinion of the International Searching Authority dated Dec. 28, 2009 for PCT/US2009/044351.

* cited by examiner

*Primary Examiner* — Lisa Caputo
*Assistant Examiner* — Punam Roy
(74) *Attorney, Agent, or Firm* — Cantor Colburn LLP

(57) ABSTRACT

Exemplary embodiments of the present invention relate to methods and devices for monitoring the flow of particulate matter within an exhaust gas stream. In one exemplary embodiment, a particulate matter sensor for an exhaust system of an engine is provided. The particulate matter sensor includes a casing having an attachment feature for mounting the particulate matter sensor to the exhaust system. The particulate matter sensor also includes an insulator disposed within the casing. The particulate matter sensor further includes a sensing rod having a hollow portion extending between a first end and a second end of the sensing rod. The first end of the sensing rod is supported by the insulator and the second end of the sensing rod extending away from the insulator. The particulate matter sensor still further includes an electrical connector assembly engaging the first end of the sensing rod. The electrical connector assembly is configured to transmit a signal generated by the sensing rod.

13 Claims, 2 Drawing Sheets

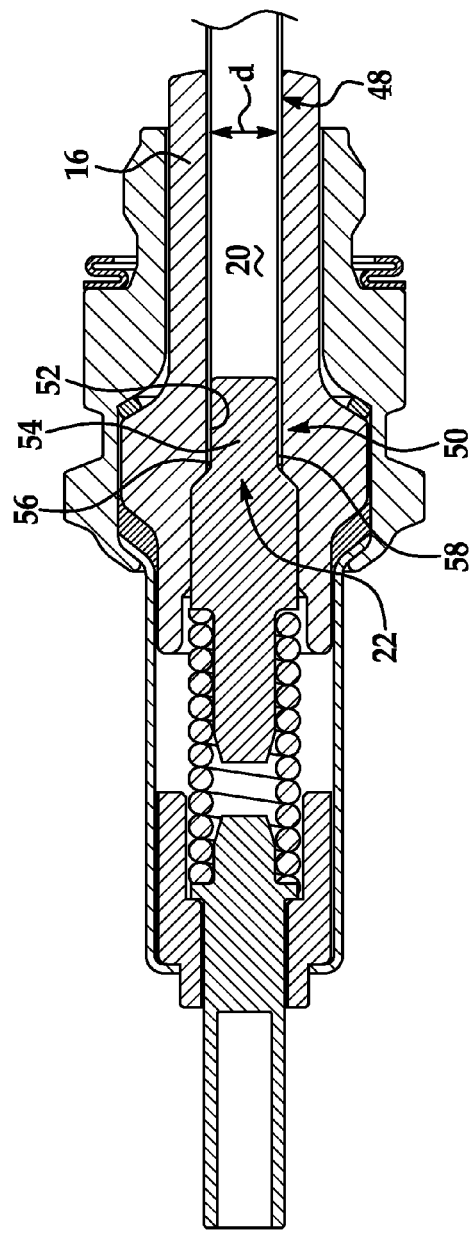
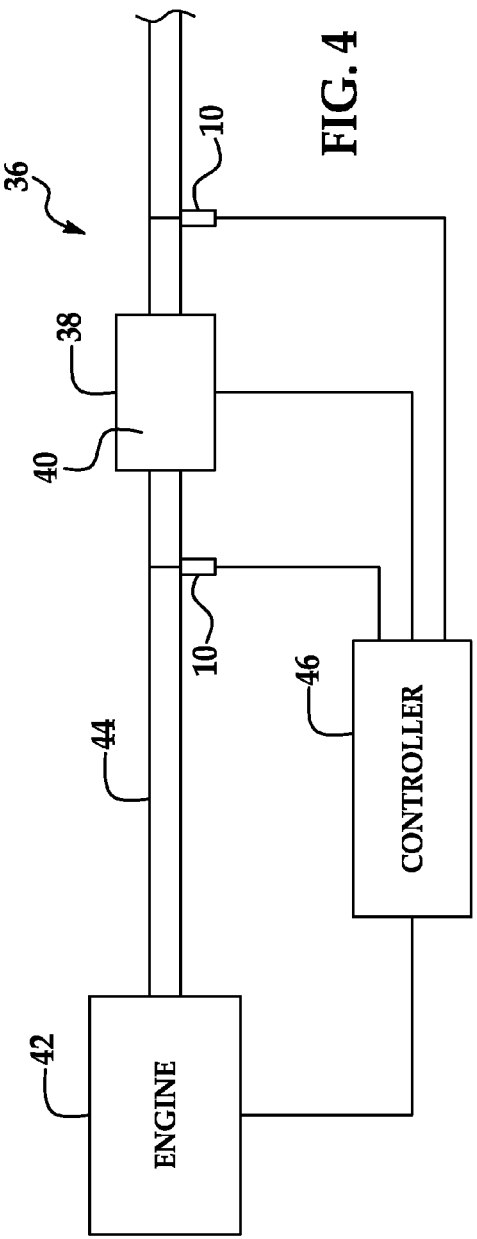
FIG. 3
FIG. 4

PARTICULATE MATTER SENSOR

CROSS REFERENCE TO RELATED APPLICATIONS

This application claims the benefit of U.S. Provisional Patent application Ser. No. 61/083,333 filed Jul. 24, 2008 the contents of which are incorporated herein by reference thereto.

This application is also a continuation-in-part U.S. patent application Ser. No. 12/467,673, filed May 18, 2009 the contents of which are incorporated herein by reference thereto.

FIELD OF THE INVENTION

Exemplary embodiments of the present invention relate to methods and devices for monitoring particulate matter flow within an exhaust gas stream.

BACKGROUND

Engine emissions have been regulated causing industries, particularly the automotive industry, to utilize particulate matter removal devices, such as filters, for reducing the amount of particulate matter expelled into the environment. Such filters are configured to remove particulate matter from the exhaust gas flow before discharge from the vehicle. In order to determine the remaining capacity of the filter, the flow rate of particulate matter through the exhaust gas stream is monitor. This monitoring is often achieved through a particulate matter sensor placed within the exhaust gas stream, wherein a signal is generated based upon an amount of particulate matter flowing across or past the sensor. However, many of these sensors fail to provide accurate readings of particulate matter flowing within an exhaust gas stream. For example, many of these sensors are not sufficiently robust to withstand forces or temperatures encountered by such sensors. Other problems with these sensors are in their inability to accurately indicate the presence of particulate matter within an exhaust gas flow due to poor signal noise ratio and other deficiencies. Other problems exist as well. Accordingly, there is a need for improved methods and devices for monitoring the flow of particulate matter within an exhaust gas stream.

SUMMARY OF THE INVENTION

Exemplary embodiments of the present invention relate to methods and devices for monitoring the flow of particulate matter within an exhaust gas stream. In one exemplary embodiment, a particulate matter sensor for an exhaust system of an engine is provided. The particulate matter sensor includes a casing having an attachment feature for mounting the particulate matter sensor to the exhaust system. The particulate matter sensor also includes an insulator disposed within the casing. The particulate matter sensor further includes a sensing rod having a hollow portion extending between a first end and a second end of the sensing rod. The first end of the sensing rod is supported by the insulator and the second end of the sensing rod extending away from the insulator. The particulate matter sensor still further includes an electrical connector assembly engaging the first end of the sensing rod. The electrical connector assembly is configured to transmit a signal generated by the sensing rod.

In another exemplary embodiment, a method of monitoring particulate matter flowing within an exhaust gas stream is provided. The method includes: supporting a hollow tube member within a casing through an insulator, the casing including an attachment feature for attachment to an exhaust component; placing the hollow tube member within the exhaust gas stream, the hollow tube member including an open end and a closed end, the closed end being disposed within the exhaust gas stream; connecting the open end of the hollow tube member to an electrical connector, the electrical connector being configured to transmit signals generated by the hollow tube member; and generating electrical signal with the hollow tube member based upon particulate matter flowing past the hollow tube member and through the exhaust gas stream.

The above features and advantages and other features and advantages of the present invention are readily apparent from the following detailed description of the best modes for carrying out the invention when taken in connection with the accompanying drawings.

BRIEF DESCRIPTION OF THE DRAWINGS

Other objects, features, advantages and details appear, by way of example only, in the following detailed description of embodiments, the detailed description referring to the drawings in which:

FIG. 3 illustrates an enlarged view of FIG. 2; and

FIG. 4 illustrates a schematic view of an exhaust control system including one or more sensors according to an exemplary embodiment of the present invention.

DETAILED DESCRIPTION OF EXEMPLARY EMBODIMENTS

Exemplary embodiments of the present invention provide methods, systems and devices for detecting and monitoring particulate matter flowing in an exhaust gas stream. In one particular exemplary embodiment, a particulate matter sensor is provided having a more robust designed and reduced cost as compared to certain prior particulate matter sensors. In one exemplary embodiment, these benefits are achieved through a reduction of material used to form the particulate matter sensor. More particularly, the particulate matter sensor includes a hollow sensing rod used to detect the particulate matter flowing through the exhaust gas stream. This configuration is particularly advantageous as certain advantageous materials used for forming sensing rods are particularly expensive. Also, in one exemplary embodiment, the hollow sensing rod is formed of a hollow tubular member providing strength to sensing rod.

Reference is made to the following U.S. Pat. Nos. 6,971, 258; 7,275,415; and 4,111,778 the contents each of which are incorporated herein by reference thereto.

Figure 1:
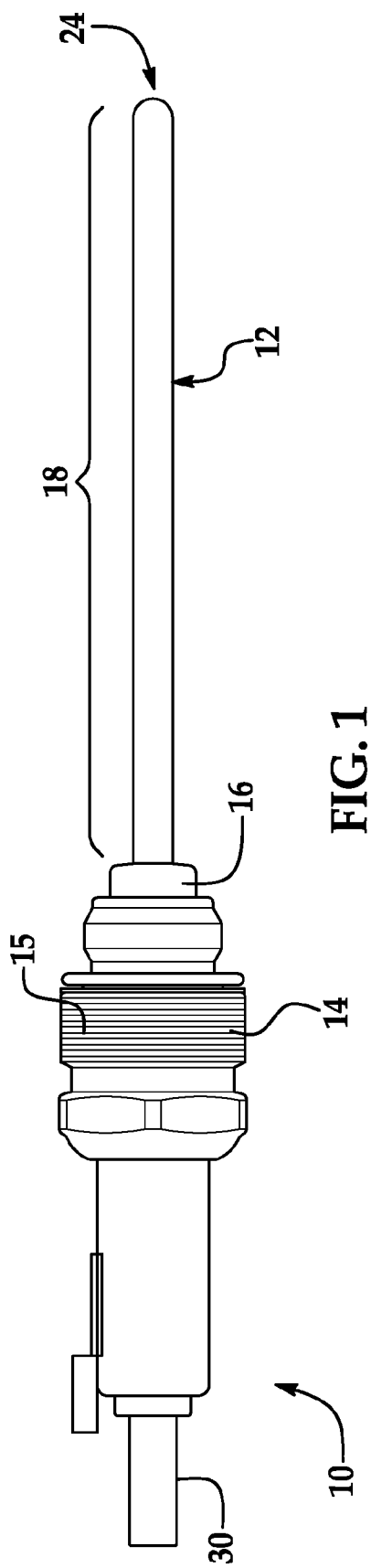
FIG. 1 illustrates an elevational view of an exemplary embodiment of a sensor according to the teachings of the present invention.
Figure 2:
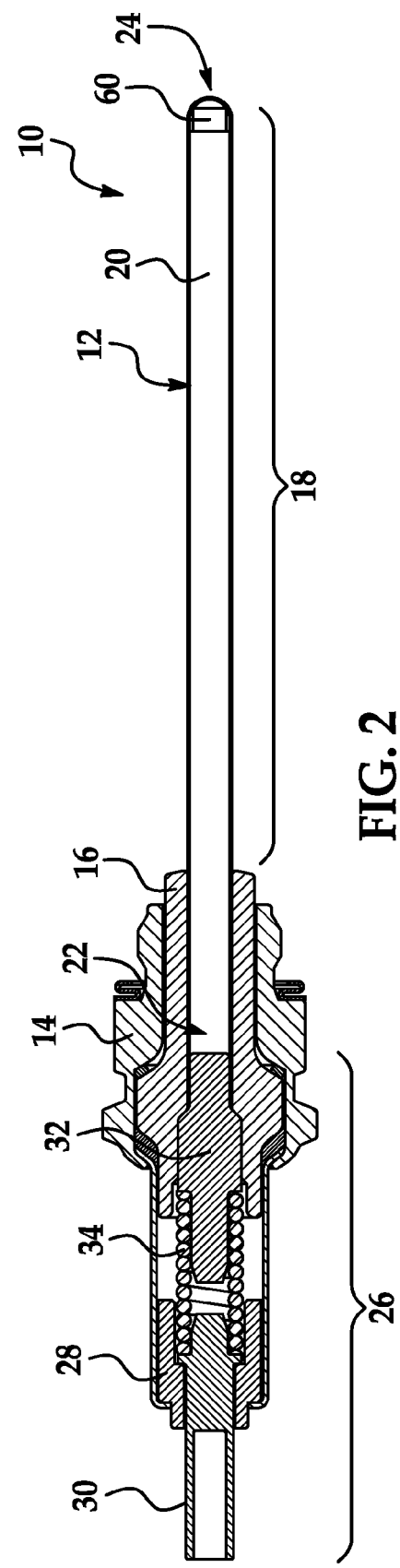
FIG. 2 illustrates a cross-sectional view of the sensor shown in FIG. 1.

In general, referring to FIGS. 1 and 2, an exemplary embodiment of improved particulate matter sensor 10 is provided. The particulate matter sensor includes a sensing rod 12 supported by a casing 14, the casing including an attachment feature 15 (such as a threaded portion) for attachment of the particulate matter sensor to an exhaust component. A first insulator 16 is disposed between sensing rod 12 and casing 14 for providing electrical insulation between the sensing rod and the casing. The sensing rod includes a probe 18 extending from casing 14 and configured for placement within an exhaust gas stream of an engine and for detecting particulate matter flowing within the stream. In one particular exemplary embodiment, the sensing rod 12 includes a hollow portion 20 extending between a first end 22 of the sensing rod and a second end 24 of the sensing rod. As the sensing rod generates signals based upon particulate matter within the exhaust gas stream, the particulate matter sensor 10 further includes a connector assembly 26 for electrically connecting the sensing rod to a signal receiver, such as a controller 46 (see FIG. 4). As with the sensing rod 12, the connector assembly 26 is supported by casing 14 and insulated from the casing through the first insulator 16 and a second insulator 28. The connector assembly 26 includes a terminal 30 for connection to the signal receiver, sensing rod connector 32 for connection to the sensing rod and an intermediate connector 34 for electrically connecting the terminal to the sensing rod.

In one embodiment, as exhaust gas flows past the sensing rod disposed in the exhaust gas or fluid stream signals are generated by the probe due to an electrical charge built up in the probe based upon the charge (e.g., electrical potential) of the particles flowing past the probe, wherein the signals are transmitted to a controller.

In operation, signals generated by the probe 18 of the sensing rod 12 are transmitted through the sensing rod connector 32, intermediate connector 34 and terminal 28 to the signal receiver.

In one exemplary operation, referring to FIG. 4, an exhaust control system 36 is providing for monitoring and removing particulate matter from an exhaust gas stream. The exhaust system includes and exhaust control device 38, such as a particulate matter filter 40, which is in fluid communication with an engine 42 through a suitable exhaust gas conduit 44. The exhaust control system 36 also includes one or more particulate matter sensors 10, located before and/or after the particulate matter filter 40. In one exemplary embodiment, as exhaust gas flows through the exhaust gas conduit 44, the total volume of particulate matter for a given time period is determined by monitoring an electrical signal across a surface of the probe 16 generated by an electrical potential of particles flowing past the probe to determine the amount of particulate matter that has flowed into the exhaust control device 40. The particulate matter sensor 10 generates signals based upon the charged particles flowing past the probe 16. The signals are received by controller 46 configured for determining the total amount of particulate matter that has flowed past the probe and into the particulate matter filter 40. Once the total volume of particulate matter reaches a predetermined level, the controller initiates regeneration of the particulate mater filter 40.

In greater detail, with reference to the exemplary embodiment shown in FIG. 2, the particulate matter sensor 10 includes a sensing rod 12 having a hollow portion 20 for reduction in the sensing rod and the overall mass of the particulate matter sensor 10. This reduction in weight not only reduces the material cost of the sensing rod portion 12 of the particulate matter sensor, but also reduces potential damage to the particulate matter sensor through vibration or other mechanical forces subjected to the cantilevered probe 18. In other words, a solid probe with the same diameter and length and corresponding sensing surface area will have much more displacement at its distal end due to vibrations or other forces. In one configuration, the sensing rod 12 comprises a hollow tube portion 48, wherein the hollow portion extends between the first end 22 of the sensing rod 12 and the second end 24 of the sensing rod. In this configuration, the sensing rod has a generally consistent cross-sectional shape and size along the length of the sensing rod 12.

Referring to FIG. 3, the first end 22 of the sensing rod 12 includes an engagement feature 50 for forming a suitable electric connection with the connector assembly 26 and more particularly the sensing rod connector 32. In this configuration, the engagement feature comprises an open end 52 of the sensing rod 12 and an extension 54 of the sensing rod connector 32. In one particular exemplary embodiment, the open end 52 of the hollow tube member 48 includes suitable dimensions and tolerances for alignment of the hollow tube member, and hence probe 18, with the sensing rod connector 32 and more particularly casing 14. This alignment provides accurate placement of the probe 18 within the exhaust gas stream for ensuring proper measurement of particulate matter flowing through the exhaust gas stream, such as done by controller 46 or otherwise. It should be appreciated that the connection between the sensing rod 12 and the connector assembly 26 may be improved through welding, adhesives or other form of bonding. In another configuration, the sensing rod 12 may be attached to the sensing rod connector 32 through mechanical attachment, such as a threaded configuration. Still other attachment configurations include brazing, laser welding or all other high temperature attachment configurations.

Similarly, engagement between the sensing rod and first insulator 16 or sensing rod connector 32 may be achieved by an opening 56 formed through the first insulator, wherein the opening has a cross-sectional shape similar to that of the cross-sectional shape of the sensing rod 12. Attachment of the sensing rod 12 to the first insulator 16, may be achieved through any suitable means. For example, in one configuration a high temperature resistant adhesive is used for bonding of the sensing rod 12 to the first insulator 16. Examples of suitable high temperature adhesives include alumina based adhesives such as Ceramabond™ 571, sold by Aremco Products Inc. of Valley Cottage, N.Y. U.S.A. and equivalents thereof In one exemplary embodiment, the sensing rod 12 comprises hollow tube member 48 that includes an inner diameter 'd,' the inner diameter being particularly suited for resisting oscillating. This is because hollow tube members are more resistant to bending as compared to sensing rods. The distance 'd' between a first side 56 and a second side 58 of the hollow tube member 48 effects resistance to oscillatory movement of the probe 18 of the sensing rod, particularly when the first end of the sensing rod is bonded or otherwise attached to the first insulator 16, sensing rod connector 32 or both. In addition, parts can be orientated/positioned accurately by using the inner diameter of the tube for positioning during plasma coating of the sensor. For example, end 22 is positioned around a reduced neck portion of sensing rod connector 32 until it abuts against a larger diameter portion of the sensing rod connector 32.

The sensing rod 12 may be formed of any suitable material for detection of particulate matter. In one configuration, the sensing rod is formed of an electrically conductive or semi-conductive material and is also capable of withstanding deleterious effects of exhaust emission (e.g., heat, corrosiveness, or otherwise). For example, the sensing rod may be formed of metal, metal alloy or otherwise. Examples of suitable metals and metal alloys include stainless steel, nickel and nickel alloys such as nickel-iron or nickel-iron-cobalt. Examples of specific suitable materials include nickel alloys non-limiting examples include Haynes® 214® or Haynes® 240®, both of which are sold by Haynes International Inc. of Kokomo, Indiana, U.S.A. In one particular exemplary embodiment, the sensing rod 12 is formed of a nickel-cobalt ferrous alloy, one non-limiting example includes those sold under the trademark name Kovar™. This material is particularly suited for detecting particulate matter but due to its relative high cost is not often used. In another particular exemplary embodiment, the sensing rod is formed of a nickel-steel alloy, such as Invar, also known generically as FeNi36 or 64FeNi. However, through the formation of a hollow tube member, the cost associated with the use of such materials is considerably reduced.

The hollow tube member 48 may be formed through any suitable means. In one exemplary embodiment, the hollow tube member 48 is formed through an extrusion process. Through this process, the hollow portion 20 of the hollow tube member is continuous. In order to prevent exhaust gas flow into the hollow tube member 18, which may negatively affect accuracy of the particulate matter sensor, and is difficult to remove during a regeneration process, it is contemplated that the particulate matter sensor 10 further includes a cap 60 for covering the hollow portion 20. More so, in one particular exemplary embodiment, cap 60 acts to form a seal between the hollow portion and surrounding exhaust gas flow. It should be appreciated that the cap may be attached through any of the bonding techniques described herein. Alternatively, or in conjunction with bonding, the cap may be mechanically attached to the hollow tube member, such as through a threaded configuration.

In one exemplary embodiment, the probe 18 or entire sensing rod 12 includes a coating for maintaining accuracy of the particulate matter sensor. Such coating may comprise a dielectric coating for preventing ions within the exhaust gas stream from forming on the probe. In one configuration, the coating comprises an aluminum oxide coating. Other coatings are possible such as Zirconium oxide, glass-based coating or otherwise.

The particulate matter sensor 10 may be used in various industries for determining a flow of particulate matter. These industries include, without limitation, automotive industry, freight industry, mass transit industry, power generating industry such as power plants or factors, or other emission producing industry. In one particularly advantageous application, the particulate matter sensor 10 is used in the automotive industry and more particularly with internal combustion engines of vehicles for monitor particulate matter generated thereby. In this configuration, the particulate matter sensor 10 is placed within the exhaust gas stream flowing through an exhaust gas conduit 44, exhaust control device 38 or otherwise, from a diesel engine, gasoline engine, hybrid engine or otherwise.

Further exemplary embodiments include monitoring particulate matter flowing within an exhaust gas stream using a sensing rod constructed in accordance with exemplary embodiments of the present invention. In one embodiment, the method includes generating signals with the particulate matter sensor based upon the presence of particulate matter flowing in the exhaust gas stream and flowing past the sensor and thus creating an electrical signal in the probe based upon the electrically charged particles or the electrical potential of the particles flowing past the sensing rod of the probe. As previously mentioned and in one exemplary embodiment, the signal is based upon a charge created in the probe based upon particulate matter flowing past the sensor. The controller receives the signals and determines at least one flow characteristic of particulate matter flowing within the exhaust gas stream such as total amount of particulate matter flowing by the sensor and into the emission control device, or volume flow rate of particulate matter or otherwise.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the present application.

What is claimed is:

1. A particulate matter sensor for an exhaust system of an engine, comprising:
   a casing having an attachment feature for mounting the particulate matter sensor to the exhaust system;
   an insulator disposed within the casing;
   a sensing rod having a hollow portion extending between a first end and a second end of the sensing rod, the first end of the sensing rod being inserted into the insulator and the second end of the sensing rod extending away from the insulator; and
   an electrical connector assembly engaging the first end of the sensing rod, wherein a portion of the first end of the sensing rod is disposed over an extension of the electrical connector assembly and wherein the portion of the first end of the sensing rod contacts an inner surface of the insulator and wherein the electrical connector assembly being configured to transmit a signal generated by the sensing rod; and
   wherein the extension of the electrical connector has a first dimension and another portion of the electrical connector has a second dimension the second dimension being greater than the first dimension and wherein the another portion contacts the insulator and the extension does not contact the insulator.

2. The particulate matter sensor of claim 1, wherein the hollow portion extends away from the first end of the sensing rod.

3. The particulate matter sensor of claim 1, wherein the first end of the sensing rod includes an opening locating the portion of the first end over the extension of the electrical connector assembly and the extension of the electrical connector assembly aligns the sensing rod with the casing.

4. The particulate matter sensor of claim 3, wherein the second end of the sensing rod is sealed to prevent fluid flow into the hollow portion of the sensing rod.

5. The particulate matter sensor of claim 1, wherein the sensing rod comprises a tube having an open first end and a closed second end and wherein the tube has a generally consistent cross-sectional shape and size along the length of the sensing rod.

6. The particulate matter sensor of claim 1, wherein the sensing rod is formed of a material comprising nickel-cobalt ferrous alloy.

7. The particulate matter sensor of claim 1, wherein the sensing rod is formed of a material comprising nickel-iron alloy.

8. The particulate matter sensor of claim 1, wherein the sensing rod further includes a dielectric coating.

9. The particulate matter sensor of claim 1, wherein the sensing rod comprises a tube having an open first end and a closed second end and wherein the tube has a generally consistent cross-sectional shape and size along the length of the sensing rod.

10. A particulate matter sensor for an exhaust system of an engine, comprising:
    a casing having an attachment feature for mounting the particulate matter sensor to the exhaust system;
    an insulator disposed within the casing;

a sensing rod having a hollow portion extending between a first end and a second end of the sensing rod, the first end of the sensing rod being inserted into the insulator and the second end of the sensing rod extending away from the insulator; and an electrical connector assembly engaging the first end of the sensing rod, wherein a portion of the first end of the sensing rod is disposed over an extension of the electrical connector assembly and wherein the portion of the first end of the sensing rod contacts an inner surface of the insulator and wherein the electrical connector assembly being configured to transmit a signal generated by the sensing rod, wherein the extension of the electrical connector is disposed at one end of the electrical connector and an opposite end of the electrical connector is electrically connected to a terminal by a connector configured as a coil spring wherein one end of the coil spring is secured to the terminal and another end of the coil spring is secured to the opposite end of the electrical connector.

11. The particulate matter sensor of claim 10, wherein the one end of the coil spring is positioned over a portion of the terminal and the another end of the coil spring is positioned over a portion of the opposite end of the electrical connector.

12. The particulate matter sensor of claim 11, wherein the extension of the electrical connector has a first dimension and another portion of the electrical connector has a second dimension the second dimension being greater than the first dimension and wherein the another portion contacts the insulator and the extension does not contact the insulator.

13. The particulate matter sensor of claim 12, wherein the sensing rod comprises a tube having an open first end and a closed second end and wherein the tube has a generally consistent cross-sectional shape and size along the length of the sensing rod.

* * * * *